United States Patent
Shao et al.

(10) Patent No.: US 11,229,707 B2
(45) Date of Patent: Jan. 25, 2022

(54) PROMOTING IMMUNE RESPONSES

(71) Applicant: National Institute of Biological Sciences, Beijing, Beijing (CN)

(72) Inventors: Feng Shao, Beijing (CN); Ping Zhou, Beijing (CN); Yang She, Beijing (CN); Huabin He, Beijing (CN); Peng Li, Beijing (CN); Jingjin Ding, Beijing (CN); Wenqing Gao, Beijing (CN)

(73) Assignee: National Institute of Biological Sciences, Beijing (CN)

( * ) Notice: Subject to any disclaimer, the term of this patent is extended or adjusted under 35 U.S.C. 154(b) by 0 days.

(21) Appl. No.: 17/022,073

(22) Filed: Sep. 15, 2020

(65) Prior Publication Data

US 2020/0405869 A1  Dec. 31, 2020

Related U.S. Application Data

(63) Continuation of application No. PCT/CN2019/090647, filed on Jun. 11, 2019.

(30) Foreign Application Priority Data

Jun. 14, 2018  (WO) ............... PCT/CN2018/091177

(51) Int. Cl.
| | |
|---|---|
| A61K 9/00 | (2006.01) |
| A61K 47/54 | (2017.01) |
| A61K 47/55 | (2017.01) |
| C07K 16/28 | (2006.01) |
| A61K 45/06 | (2006.01) |

(52) U.S. Cl.
CPC ............ *A61K 47/549* (2017.08); *A61K 47/55* (2017.08); *C07K 16/2818* (2013.01); *A61K 45/06* (2013.01)

(58) Field of Classification Search
CPC ...................................................... A61K 47/55
See application file for complete search history.

(56) References Cited

U.S. PATENT DOCUMENTS

2020/0230219 A1* 7/2020 Nistor ..................... A61K 35/13

FOREIGN PATENT DOCUMENTS

| EP | 2017281 | 9/2014 | |
|---|---|---|---|
| WO | 2019080898 | 6/2007 | |
| WO | WO-2016054745 A1 * | 4/2016 | ........... C12Q 1/6876 |

OTHER PUBLICATIONS

Gaudet, Heptose Sounds the Alarm: Innate Sensing of a Bacterial Sugar Stimulates Immunity, PLOS Pathogens, 2016, 1/1-6/6. (Year: 2016).*
ISR-WO of PCT/CN2019/090647.
EP Comm re EP App. No. 19818829.4.
Gaudet et al., Science 348 (6240) 1251-5, Jul. 12, 2015, Cytosolic detection of the bacterial metabolite HBP activates TIFA-dependent innate immunity.
Zhou et al. Nature 561, 122-126 (2018), Alpha-kinase 1 is a cytosolic innate immune receptor for bacterial ADP-heptose.

* cited by examiner

*Primary Examiner* — Paul W Dickinson
(74) *Attorney, Agent, or Firm* — Richard Aron Osman

(57) ABSTRACT

Pharmaceutical compositions comprise a 1-ADP-heptose conjugate and may include an immunogen or an immune checkpoint inhibitor, and are used to promote an immune response.

16 Claims, 1 Drawing Sheet

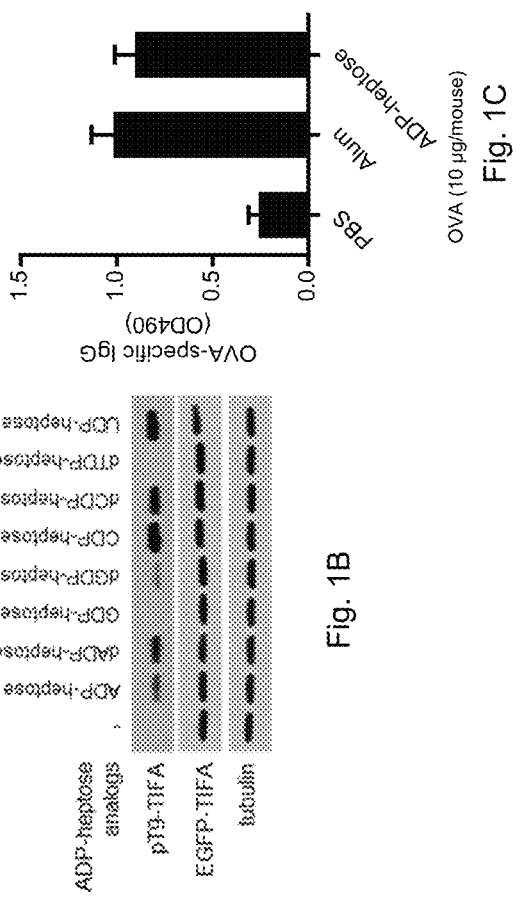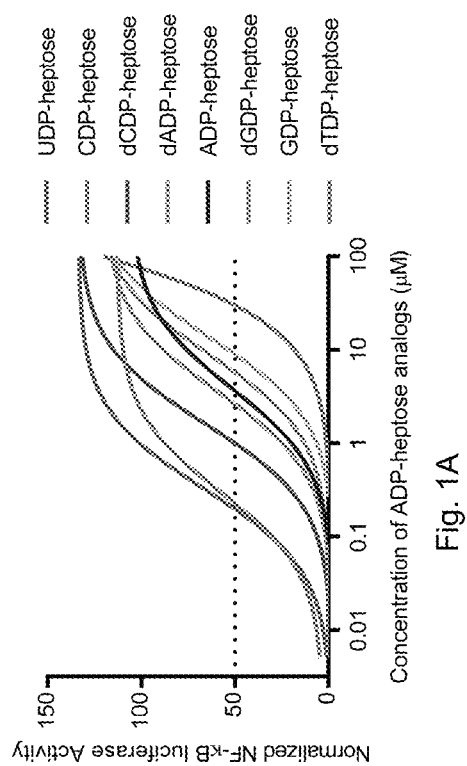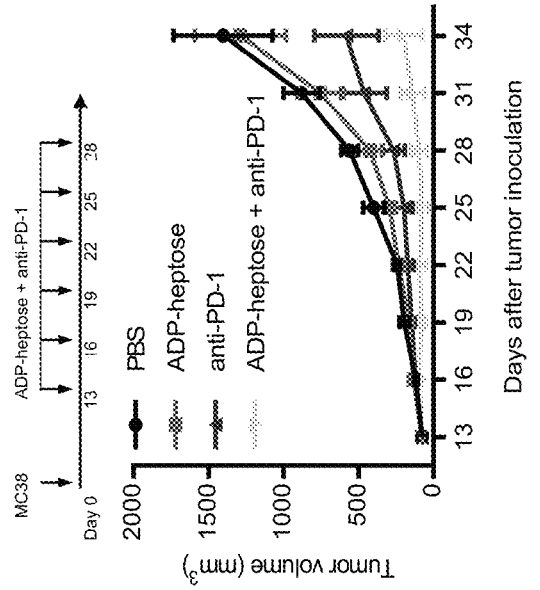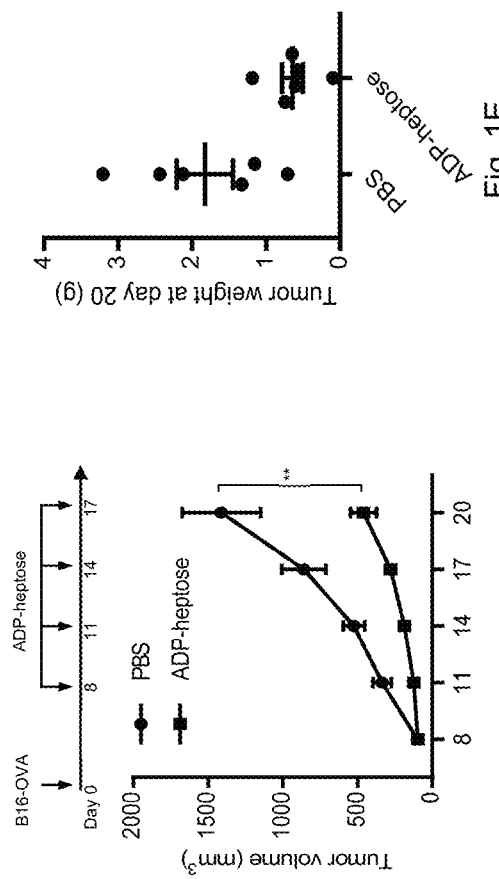

PROMOTING IMMUNE RESPONSES

INTRODUCTION

Many diseases and pathologies are associated with a compromised immune system and an increased susceptibility to infectious agents. Patients undergoing surgery, radiation or chemotherapy, and those suffering from autoimmune or other immune deficiency diseases have elevated risk of developing pathological conditions resulting from infection Immune activating strategies can be used to induce immune responses to prevent or combat infection.

Vaccines are widely used to prevent or treat infection by many infectious organisms, including bacterial, viruses and fungi, and a variety of vaccines and immunotherapies have been developed to treat cancer, and many strategies and adjuvants have been used to enhance their efficacies.

There is ongoing need to develop further treatment and prevention options against infections caused by infectious agents, cancerous cells and immune or inflammatory diseases.

Relevant literature includes WO2016054745 and Gaudet et al. *Science* 348, 1251-1255 (2015).

SUMMARY OF THE INVENTION

The invention provides methods of promoting an immune response and corresponding pharmaceutical compositions.

In an aspect the invention provides a method of promoting an immune response comprising administering to a person in need thereof a composition comprising a 1-ADP-heptose conjugate.

In embodiments
- the heptose is of configuration: L/D-glycero-α/β-L/D-manno/gluco/galacto-heptose.
- the heptose is of configuration: L/D-glycero-α/β-L/D-manno-heptose.
- the heptose is of configuration: L/D-glycero-α/β-D-manno-heptose.
- the heptose is of configuration: L/D-glycero-β-D-manno-heptose.
- the heptose is of configuration:

| | |
|---|---|
| L-glycero-β-D-gluco-heptose | L-glycero-β-L-galacto-heptose |
| D-glycero-β-D-gluco-heptose | D-glycero-β-L-galacto-heptose |
| L-glycero-α-D-gluco-heptose | L-glycero-α-L-galacto-heptose |
| D-glycero-α-D-gluco-heptose | D-glycero-α-L-galacto-heptose |
| L-glycero-β-L-gluco-heptose | L-glycero-β-D-manno-heptose |
| D-glycero-β-L-gluco-heptose | D-glycero-β-D-manno-heptose |
| L-glycero-α-L-gluco-heptose | L-glycero-α-D-manno-heptose |
| D-glycero-α-L-gluco-heptose | D-glycero-α-D-manno-heptose |
| L-glycero-β-D-galacto-heptose | L-glycero-β-L-manno-heptose |
| D-glycero-β-D-galacto-heptose | D-glycero-β-L-manno-heptose |
| L-glycero-α-D-galacto-heptose | L-glycero-α-L-manno-heptose or |
| D-glycero-α-D-galacto-heptose | D-glycero-α-L-manno-heptose; |

- the conjugate is a 1-ADP-heptose-7-phosphate.
- the method further comprises administering to the person an immunogen, preferably comprising an antigen of a bacterium, virus, parasite or cancer cell.
- the method further comprises administering to the person an immune checkpoint inhibitor, preferably comprising a therapeutic antibody specific for:
  Adenosine A2A receptor (A2AR);
  Cluster of Differentiation 276 (CD276; B7-H3);
  B and T Lymphocyte Attenuator (BTLA; CD272;
  Cytotoxic T lymphocyte-associated protein 4 (CTLA-4);
  Indoleamine 2,3-dioxygenase (IDO);
  Killer immunoglobulin-like receptor (KIR);
  Lymphocyte-activation gene 3 (LAG-3; CD223);
  Programmed death protein 1 (PD-1) or programmed death ligand 1 or 2 (PD-L1 or PD-L2);
  T cell immunoglobulin mucin 3 (TIM-3); or
  V-domain Ig suppressor of T cell activation (VISTA);
  the checkpoint inhibitor is a therapeutic antibody that is a PD-L1 inhibitor, such as durvalumab, atezolizumab or avelumab; or a CTLA-4 inhibitors such as tremelimumab or tremelimumab;
  the method further comprises administering to the person the immunogen or immune checkpoint inhibitor, wherein the composition comprises the immunogen or the inhibitor.

In an aspect the invention provides an immune response promoting pharmaceutical composition comprising a 1-ADP-heptose conjugate.

In embodiments:
- the composition further comprises an immunogen or an immune checkpoint inhibitor.
- the composition is in unit dosage form.

The invention encompasses all combinations of the particular embodiments recited herein.

BRIEF DESCRIPTION OF THE DRAWINGS

FIG. 1A. ADP-heptose and its analogs (UDP-heptose, CDP-heptose, dCDP-heptose, dADP-heptose, dGDP-heptose, GDP-heptose, and dTDP-heptose) activated NF-κB in 293T cells in a dose-dependent manner NF-κB activation was measured by luciferase reporter activity.

FIG. 1B. ADP-heptose and its analogs induced TIFA phosphorylation in 293T cells. 293T cells stably expressing EGFP-TIFA were treated with ADP-heptose analogs (5 μM) for 5 hours, and analyzed by anti-pT9-TIFA immunoblot.

FIG. 1C. ADP-heptose exhibited adjuvant activity in vivo to elevate the serum ovalbumin (OVA)-specific IgG production. C57BL/6N mice (8 mice per group) were immunized intramuscularly with 10 μg OVA mixed with PBS, alum (2 mg/mouse), or ADP-heptose (0.5 mg/mouse). After 21 days, serum titers of OVA-specific IgG were measured by ELISA.

FIG. 1D and FIG. 1E. Inhibition of B16-OVA tumor growth by posttumor treatment with ADP-heptose. C57BL/6N mice (n=6 mice per group) were injected subcutaneously with 2×10⁵ B16-OVA melanoma cells on day 0. ADP-heptose (0.5 mg/mouse) was administered on day 8, 11, 14, and 17 after tumor inoculation by intratumor injection. Tumor volume (D) and tumor weight (E).

FIG. 1F. Inhibition of MC38 tumor growth by posttumor treatment with ADP-heptose and checkpoint blockade. C57BL/6N mice (n=6 mice per group) were injected subcutaneously with 2×10⁵ MC38 colorectal adenocarcinoma cells on day 0. ADP-heptose (0.5 mg/mouse, intratumor injection) and anti-PD-1 antibody (40 ug/mouse, intraperitoneal injection) was administered on day 13, 16, 19, 22, 25, and 28 after tumor inoculation.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results. The invention provides myriad embodiments.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The immunogen may be an antigen of infectious agent, such as infectious bacterial, viral or parasitic pathogens, including Gram-negative bacterial pathogens belonging to the genus *Neisseria* (including *Neisseria meningitidis, Neisseria gonorrohoeae*), *Escherichia* (including *Escherichia coli*), *Klebsiella* (including *Klebsiella pneumoniae*), *Salmonella* (including *Salmonella typhimurium*), *Shigella* (including *Shigella dysenteriae, Shigella flexneri, Shigella sonnei*), *Vibrio* (including *Vibrio cholerae*), *Helicobacter* (including *Helicobacter pylori*), *Pseudomonas* (including *Pseudomonas aeruginosa*), *Burkhoideria* (including *Burkhoideria multivorans*), *Haemophilus* (including *Haemophilus influenzae*), *Moraxella* (including *Moraxella catarrhalis*), *Bordetella* (including *Bordetella pertussis*), *Francisella* (including *Francisella tularensis*), *Pasteurella* (including *Pasteurella multocida*), *Legionella* (including *Legionella pneumophila*), *Borrelia* (including *Borrelia burgdorferi*), *Campylobacter* (including *Campylobacter jejuni*), *Yersinia* (including *Yersinia pestis* and *Yersinia enterocolitica*), *Rickettsia* (including *Rickettsia rickettsii*), *Treponema* (including *Treponema pallidum*), *Chlamydia* (including *Chlamydia trachomatis, Chlamydia pneumoniae*) and *Brucella* spp., and including Gram positive bacterial pathogens belonging to the genus *Staphylococcus* (including *Staphylococcus aureus*), *Streptococcus* (including *Streptococcus pneumoniae, Streptococcus pyogenes*), *Listeria* (including *Listeria monocytogenes*), *Corynebacterium* (including *Corynebacterium diphtheriae*), *Enterococcus* (including *Enterococcus faecalis*), *Clostridium* spp., and *Mycobacterium* (including *Mycobacterium tuberculosis, Mycobacterium leprae, Mycobacterium avium*).

Immunogens or antigens may also be from pathogenic viruses including Adenoviridae (including Adenovirus), Herpesviridae (including Epstein-Barr virus, Herpes Simplex Viruses, Cytomegalovirus, Varicella Zoster virus), Papillomviridae, Poxviridae (including Papillomavirus), Hepadnaviridae (including Hepatitis B virus), Parvoviridae, Astroviridae, Caliciviridae, Picornaviridae (including Coxsackievirus, Hepatitis A virus, Poliovirus), Coronaviridae, Flaviviridae (including Hepatitis C virus, Dengue virus), Togaviridae (including Rubella virus), Hepeviridae, Retroviridae (including HIV), Orthomyxoviridae (including influenza virus, Arenaviridae, Bunyaviridae, Filoviridae, Paramyxoviridae (including Measles virus, Mumps virus, Parainfluenza virus, Respiratory Syncytial virus), Rhabdoviridae (including Rabies virus) or Reoviridae.

Immunogens or antigens may also be from pathogenic fungal infections including those caused by *Candida, Aspergillus, Cryptococcus, Histoplasma, Pneumocystis*, or *Coccidioides*. Vaccines may also target parasitic pathogens including *Leishmania, Plasmodium, Toxoplasma, Trypanosoma* and *Schistosoma*.

The immunogen or antigen may be from a protein or other antigens expressed on the subject's own cells, such as a tumor antigen or cancer antigen, to stimulate an immune response against the pathogenic cells or tissues. In one embodiment, the compositions may be introduced directly into a tumor to increase the immune response against the tumor. The immunogen can be administered as part of a vaccine formulation.

The methods and compositions may employ the compounds in any suitable form and dosage unit, including salts, prodrugs, stereoisomers, amorphous forms, etc.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug is a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, diastereomers, geometric isomers and individual isomers are all intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

The subject compounds may be employed alone or in combination with other therapeutic agents. Combination therapies thus comprise the administration of at least one pharmaceutically acceptable crystalline or amorphous form of the compounds and at least one other therapeutically active agent. The subject compounds and the other therapeutically active agent(s) may be administered together in a single pharmaceutical composition or separately and, when administered separately this may occur simultaneously or sequentially in any order. The amounts of the subject compounds and the other therapeutically active agent(s) and the relative timings of administration will be selected in order to achieve the desired combined therapeutic effect. Thus in a further aspect, there is provided a combination comprising a pharmaceutically acceptable crystalline or amorphous form of the compounds together with one or more other therapeutically active agents.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg.

For use in therapy, the compounds of the invention will be normally, but not necessarily, formulated into a pharmaceutical composition, or administration unit, prior to administration to a patient. Accordingly, the invention also is directed to a pharmaceutical composition comprising a compound of the invention and one or more pharmaceutically acceptable excipients. The invention also is directed to an administration unit comprising a compound of the invention and one or more pharmaceutically acceptable excipients.

The pharmaceutical compositions or administration units of the invention may be prepared and packaged in bulk form wherein an effective amount of a compound of the invention can be extracted and then given to the patient such as with powders, syrups, and solutions for injection. Alternatively, the pharmaceutical compositions or administration units of the invention may be prepared and packaged in unit dosage form. For oral application, for example, one or more tablets or capsules may be administered. A dose of the pharmaceutical composition contains at least a therapeutically effective amount of a compound of the invention. When prepared in unit dosage form, the pharmaceutical compositions or administration units may contain from 1 mg to 1000 mg of a subject compound.

As provided herein, unit dosage forms (pharmaceutical compositions or administration units) containing from 1 mg to 1000 mg of compound may be administered one, two, three, or four times per day, preferably one, two, or three times per day, and more preferably, one or two times per day.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation. Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (supra). Accordingly, another embodiment of this invention is a method of preparing a pharmaceutical composition or administration unit comprising the step of admixing a pharmaceutically acceptable crystalline form of a subject compound with one or more pharmaceutically acceptable excipients.

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

Alpha-Kinase 1 is a Cytosolic Innate Immune Receptor for Bacterial 1-ADP-Heptose Immune detection of pathogen-associated molecular patterns (PAMPs) by pattern recognition receptors, which often activates the proinflammatory NF-κB signaling, determines antimicrobial defenses. Known bacterial PAMPs are restricted to a few types of structural molecules or nucleotide second messengers. Previous studies show that the type III secretion system (T3SS) in $Yersinia$ and other bacterial pathogens can activate host NF-κB signaling. Here we combined transposon screen in $Y.\ pseudotuberculosis$ and biochemical analyses, and identified a sugar metabolite 1-ADP-β-D-manno-Heptose (ADP-Hep) that mediates the T3SS-dependent NF-κB activation and inflammatory cytokine production. ADP-Hep but not its biosynthetic precursor D-glycero-β-D-manno Heptose 1,7-bisphosphate (HBP) could enter host cytosol on its own, leading to NF-kB activation as well as cytokines induction (such as interleukin-8) in THP-1 and 293T cells. This allowed us to perform genome-wide CRISPR/Cas9 screens to identify the alpha-kinase 1 (ALPK1)-TIFA axis being required for ADP-Hep-induced NF-κB activation. ALPK1 N-terminal domain (NTD) directly binds to ADP-Hep, which stimulates the NTD-bound C-terminal kinase domain to phosphorylate TIFA and induce its oligomerization. Crystal structure of ALPK1-NTD/ADP-Hep complex revealed atomic mechanism of this ligand/receptor recognition. HBP can be converted into ALPK1 activation-competent ADP-Heptose 7-P by host-derived adenylyltransferases, explaining NF-κB activation observed with HBP transfected into host cells. Injection of ADP-Hep (but not the cell-impermeable HBP) or bacterial infection induces robust inflammatory responses in mice in an Alpk1-dependent manner ADP-Hep and ALPK1 are a new and generic pattern recognition pathway in antibacterial immunity.

ADP-Hep Alone or During Bacterial Infection Induces Robust Immune Responses in an Alpk1-Dependent Manner To investigate whether ADP-Hep alone could stimulate innate immune responses in vivo, a mouse dorsal air pouch model established to assess acute inflammation was employed (Gaudet et al. $Science$ 348, 1251-1255 (2015).

Injection of chemically synthesized ADP-LD-Hep into the air pouch induced massive neutrophil recruitment into the pouch. In contrast, the same amount of chemically synthesized HBP failed to increase the number of air-pouch neutrophils, agreeing with the inability of HBP to enter mammalian cells. We then performed a multiplex immunoassay for 36 cytokines in both the air-pouch washes and the sera of injected mice. A series of proinflammatory cytokines and chemokines, including IL-6, TNFα, C—X—C motif chemokine 10 (IP-10/CXCL10), monocyte chemoattractant protein-1 and 3 (MCP-1/3), IFNγ, GM-CSF, MIP-1α and β, and RANTES, were highly elevated in air pouches injected with ADP-LD-Hep compared with those of the saline control. ADP-LD-Hep also increased the level of keratinocyte-derived chemokine (GRO-α/KC/CXCL1), IP-10 and MCP-1 in the sera. In contrast to ADP-LD-Hep, injection of HBP into the air pouch did not affect local and systemic productions of these inflammatory cytokines and chemokines that are known targets of NF-κB-mediated transcription. Thus, ADP-Hep but not HBP alone can potently activate innate immune responses in mice.

1-ADP-L/D-Glycero-α/β-L/D-Manno/Gluco/Galacto-Heptose Conjugates Promote Robust Immune Responses To confirm that 1-ADP-heptoses and 1-ADP-heptose-7-phosphates can stimulate innate immune responses in vivo, a mouse dorsal air pouch model established to assess acute inflammation was employed (Gaudet, et al. $Science$ 348, 1251-1255 (2015).

Injection of 1-ADP-heptoses and 1-ADP-heptose-7-phosphates into the air pouch induces neutrophil recruitment into the pouch. Performing the same multiplex immunoassay for 36 cytokines in both the air-pouch washes and the sera of injected mice, a series of proinflammatory cytokines and chemokines, including IL-6, TNFα, C—X—C motif chemokine 10 (IP-10/CXCL10), monocyte chemoattractant protein-1 and 3 (MCP-1/3), IFNγ, GM-CSF, MIP-1α and β, and RANTES, are highly elevated in air pouches injected with 1-ADP-heptoses and 1-ADP-heptose-7-phosphates compared with those of the saline control. 1-ADP-heptoses and 1-ADP-heptose-7-phosphates also increase the level of keratinocyte-derived chemokine (GRO-a/KC/CXCL1), IP-10 and MCP-1 in the sera. Compounds 1-24 (Table 1) and compounds 25-38 (Table 2) each demonstrate enhanced neutrophil recruitment and cytokine/chemokine inducement ranging from about 30-200% those of ADP-LD-Hep; hence, these 1-ADP-L/D-glycero-α/β-L/D-manno/gluco/galacto-heptose conjugates promote robust immune responses in vivo.

Our results demonstrate, inter alia, that we have identified ADP-heptose analogs (including UDP-heptose, CDP-heptose, dCDP-heptose, dADP-heptose, dGDP-heptose, GDP-heptose, and dTDP-heptose) which can activate NF-kB and induce TIFA phosphorylation in 293T cells; ADP-heptose exhibited adjuvant activity in vivo to elevate the serum antigen-specific IgG production; ADP-heptose intratumor injection can inhibit the B16-OVA tumor growth; and ADP-heptose combined with anti-PD-1 antibody can inhibit the MC38 tumor growth; see FIGS. 1A-1F.

TABLE 1

Active 1-ADP-heptoses

| | |
|---|---|
| 1 | 1-ADP-L-glycero-β-D-gluco-heptose |
| 2 | 1-ADP-D-glycero-β-D-gluco-heptose |
| 3 | 1-ADP-L-glycero-α-D-gluco-heptose |
| 4 | 1-ADP-D-glycero-α-D-gluco-heptose |
| 5 | 1-ADP-L-glycero-β-L-gluco-heptose |
| 6 | 1-ADP-D-glycero-β-L-gluco-heptose |
| 7 | 1-ADP-L-glycero-α-L-gluco-heptose |
| 8 | 1-ADP-D-glycero-α-L-gluco-heptose |
| 9 | 1-ADP-L-glycero-β-D-galacto-heptose |
| 10 | 1-ADP-D-glycero-β-D-galacto-heptose |
| 11 | 1-ADP-L-glycero-α-D-galacto-heptose |
| 12 | 1-ADP-D-glycero-α-D-galacto-heptose |
| 13 | 1-ADP-L-glycero-β-L-galacto-heptose |
| 14 | 1-ADP-D-glycero-β-L-galacto-heptose |
| 15 | 1-ADP-L-glycero-α-L-galacto-heptose |
| 16 | 1-ADP-D-glycero-α-L-galacto-heptose |
| 17 | 1-ADP-L-glycero-β-D-manno-heptose |
| 18 | 1-ADP-D-glycero-β-D-manno-heptose |
| 19 | 1-ADP-L-glycero-α-D-manno-heptose |
| 20 | 1-ADP-D-glycero-α-D-manno-heptose |
| 21 | 1-ADP-L-glycero-β-L-manno-heptose |
| 22 | 1-ADP-D-glycero-β-L-manno-heptose |
| 23 | 1-ADP-L-glycero-α-L-manno-heptose |
| 24 | 1-ADP-D-glycero-α-L-manno-heptose |

TABLE 2

Active 1-ADP-heptose-7-phosphates

| | |
|---|---|
| 25 | 1-ADP-L-glycero-β-D-gluco-heptose-7P |
| 26 | 1-ADP-D-glycero-β-D-gluco-heptose-7P |
| 27 | 1-ADP-L-glycero-α-D-gluco-heptose-7P |
| 28 | 1-ADP-D-glycero-α-D-gluco-heptose-7P |
| 29 | 1-ADP-L-glycero-β-L-gluco-heptose-7P |
| 30 | 1-ADP-D-glycero-β-L-gluco-heptose-7P |
| 31 | 1-ADP-L-glycero-α-L-gluco-heptose-7P |
| 32 | 1-ADP-D-glycero-α-L-gluco-heptose-7P |
| 33 | 1-ADP-L-glycero-β-D-galacto-heptose-7P |
| 34 | 1-ADP-D-glycero-β-D-galacto-heptose-7P |
| 35 | 1-ADP-L-glycero-α-D-galacto-heptose-7P |
| 36 | 1-ADP-D-glycero-α-D-galacto-heptose-7P |
| 37 | 1-ADP-L-glycero-β-L-galacto-heptose-7P |
| 38 | 1-ADP-D-glycero-β-L-galacto-heptose-7P |
| 39 | 1-ADP-L-glycero-α-L-galacto-heptose-7P |
| 40 | 1-ADP-D-glycero-α-L-galacto-heptose-7P |
| 41 | 1-ADP-L-glycero-β-D-manno-heptose-7P |
| 42 | 1-ADP-D-glycero-β-D-manno-heptose-7P |
| 43 | 1-ADP-L-glycero-α-D-manno-heptose-7P |
| 44 | 1-ADP-D-glycero-α-D-manno-heptose-7P |
| 45 | 1-ADP-L-glycero-β-L-manno-heptose-7P |
| 46 | 1-ADP-D-glycero-β-L-manno-heptose-7P |
| 47 | 1-ADP-L-glycero-α-L-manno-heptose-7P |
| 48 | 1-ADP-D-glycero-α-L-manno-heptose-7P |

What is claimed is:

1. A method of promoting an Alpk1-dependent immune response comprising: administering to a person in need thereof a composition comprising a 1-ADP-heptose conjugate that is a 1-ADP-heptose-7-phosphate.

2. The method of claim 1 wherein the heptose is of configuration:
L/D-glycero-α/β-L/D-manno/gluco/galacto-heptose.

3. The method of claim 1 wherein the heptose is of configuration:
L/D-glycero-α/β-L/D-manno-heptose.

4. The method of claim 1 wherein the heptose is of configuration:
L/D-glycero-α/β-D-manno-heptose.

5. The method of claim 1 wherein the heptose is of configuration:
L/D-glycero-β-D-manno-heptose.

6. The method of claim 1 further comprising administering to the person an immunogen.

7. The method of claim 1 further comprising administering to the person an immunogen comprising an antigen of a bacterium, virus, parasite or cancer cell.

8. The method of claim 1 further comprising administering to the person an immune checkpoint inhibitor.

9. The method of claim 1 further comprising administering to the person an immune checkpoint inhibitor comprising a therapeutic antibody specific for:
Adenosine A2A receptor (A2AR);
Cluster of Differentiation 276 (CD276; B7-H3);
B and T Lymphocyte Attenuator (BTLA; CD272;
Cytotoxic T lymphocyte-associated protein 4 (CTLA-4);
Indoleamine 2,3-dioxygenase (IDO);
Killer immunoglobulin-like receptor (KIR);
Lymphocyte-activation gene 3 (LAG-3; CD223);
Programmed death protein 1 (PD-1) or programmed death ligand 1 or 2 (PD-L1 or PD-L2);
T cell immunoglobulin mucin 3 (TIM-3); or
V-domain Ig suppressor of T cell activation (VISTA).

10. The method of claim 1 further comprising administering to the person an immune checkpoint inhibitor comprising a therapeutic antibody specific for:
Programmed death protein 1 (PD-1).

11. The method of claim 1 further comprising the step of detecting a resultant immune response.

12. The method of claim 6 further comprising the step of detecting a resultant immunogen-specific immune response.

13. The method of claim 7 further comprising the step of detecting a resultant increase in serum antigen-specific IgG production.

14. The method of claim 7 wherein the antigen is a cancer cell antigen, and the person has a tumor, the method further comprising the step of detecting a resultant decrease in tumor size.

15. The method of claim 8 wherein the person has a tumor, the method further comprising the step of detecting a resultant decrease in tumor size.

16. The method of claim 9 wherein the person has a tumor, the method further comprising the step of detecting a resultant decrease in tumor size.

* * * * *